US006828329B2

United States Patent
Cai et al.

(10) Patent No.: US 6,828,329 B2
(45) Date of Patent: Dec. 7, 2004

(54) ARYL FUSED SUBSTITUTED 4-OXY-PYRIDINES

(75) Inventors: Guolin Cai, Thousand Oaks, CA (US); Pamela Albaugh, Carmel, IN (US); Jun Yuan, Guilford, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/892,024

(22) Filed: Jun. 26, 2001

(65) Prior Publication Data

US 2002/0035121 A1 Mar. 21, 2002

Related U.S. Application Data

(60) Provisional application No. 60/214,125, filed on Jun. 26, 2000.

(51) Int. Cl.[7] .................... A61K 31/44; C07D 515/02
(52) U.S. Cl. ...................... 514/301; 546/114
(58) Field of Search .................. 546/114; 514/301; 200/828

(56) References Cited

U.S. PATENT DOCUMENTS

| 4,728,647 A | 3/1988 | Benavides et al. |
| 5,017,576 A | 5/1991 | Dubroeucq et al. |
| 5,326,868 A | 7/1994 | Thurkauf et al. |

FOREIGN PATENT DOCUMENTS

| EP | 205375 | 12/1986 |
| EP | 362006 | 4/1990 |
| WO | WO 92/06094 | 4/1990 |
| WO | WO 94/02145 | 2/1994 |
| WO | WO 99/37303 | 1/1999 |
| WO | WO 99/29319 | 6/1999 |
| WO | WO 99/43681 | 9/1999 |
| WO | WO 99/43682 | 9/1999 |
| WO | WO 99/47131 | 9/1999 |
| WO | WO 99/47142 | 9/1999 |
| WO | WO 99/47171 | 9/1999 |
| WO | WO 99/65904 | 12/1999 |

OTHER PUBLICATIONS

Ho et. al., "Heterocyclic Monoazo Dyes Derived from 3–Cyano–2(1H)–Pyridinethiones. Part 1: 3–(Aryl or Hetaryl)azo–Thieno[2,3 b]pyridine Derivatives", Dyes and Pigments, vol. 2, No. 2, pp. 117–129.*

Da–Rocha et al., (1997) Journal of Psychopharmacology 11(3):211–218.
Le Ad, et al., (1996) Alcohol and Alcohol 31 (Suppl 1):27–32.
Smith et al., (1998) American Journal of Psychiatry 155(10):1339–1324.
White G. et al., (1995) Neuroreport 6(9):1313–1316.
International Search Report for International Application PCT/US 01/41146.

* cited by examiner

Primary Examiner—Joseph K. McKane
Assistant Examiner—Binta Robinson
(74) Attorney, Agent, or Firm—McDonnell Boehnen Hulbert & Berghoff LLP

(57) ABSTRACT

Disclosed are compounds of the formula:

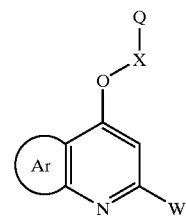

wherein X, Q, W and

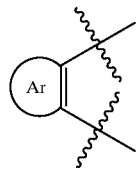

are as defined herein. These compounds are agonists, antagonists or inverse agonists for $GABA_A$ brain receptors or prodrugs of agonists, antagonists or inverse agonists for $GABA_A$ brain receptors and are therefore useful in the diagnosis and treatment of anxiety, depression, Down Syndrome, sleep and seizure disorders, overdose with benzodiazepine drugs and for enhancement of memory. Pharmaceutical compositions, including packaged pharmaceutical compositions, are further provided. Compounds of the invention are also useful as probes for the localization of $GABA_A$ receptors in tissue samples.

18 Claims, No Drawings

ARYL FUSED SUBSTITUTED 4-OXY-PYRIDINES

BACKGROUND OF THE INVENTION

This application claims priority of U.S. Provisional Application Ser. No. 60/214,125, filed Jun. 26, 2000, the disclosure of which is incorporated herein in its entirety.

FIELD OF THE INVENTION

This invention relates to substituted 4-oxy-pyridines and more specifically to such compounds that bind to the benzodiazepine site of $GABA_A$ receptors. This invention also relates to pharmaceutical compositions comprising such compounds and to the use of such compounds in the treatment of central nervous system (CNS) diseases.

DESCRIPTION OF THE RELATED ART

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits. Evidence such as message distribution, genome localization and biochemical study results suggest that the major naturally occurring receptor combinations are $\alpha_1\beta_2\gamma_2$, $\alpha_2\beta_3\gamma_2$, $\alpha_3\beta_3\gamma_2$, and $\alpha_5\beta_3\gamma_2$ (Mohler et. al. Neuroch. Res. 1995; 20(5): 631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, 6th ed., 1991, pp. 145–148, Oxford University Press, New York).

Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of other CNS active compounds. For example, there is evidence that selective serotonin reuptake inhibitors (SSRIs) may show greater antidepressant activity when used in combination with $GABA_A$ selective ligands than when used alone.

Certain 4-oxyquinoline derivatives have been described as being useful as anxiolytics, hpnotics, anticonvulsants, and antiepileptics. See, for example, European Patent Applications EP 362006 and EP 205375.

SUMMARY OF THE INVENTION

This invention provides substituted 4-oxy-pyridine derivatives that bind to the benzodiazepine site of the $GABA_A$ receptor, including human $GABA_A$ receptors.

Thus, the invention provides compounds of Formula I and Formula II (shown below), and pharmaceutical compositions comprising compounds of Formula I and Formula II.

The invention further comprises methods of treating patients suffering from CNS disorders with a therapeutically effective amount of a compound of the invention. The patient may be a human or other mammal. Treatment of humans, domesticated companion animals (pet) or livestock animals suffering from CNS disorders with a therapeutically effective amount of a compound of the invention is encompassed by the invention.

In a separate aspect, the invention provides a method of potentiating the actions of other CNS active compounds. This method comprises administering an effective amount of a compound of the invention with another CNS active compound.

Additionally this invention relates to the use of the compounds of the invention as probes for the localization of $GABA_A$ receptors in tissue sections.

Accordingly, in a broad aspect, the invention provides compounds of Formula I:

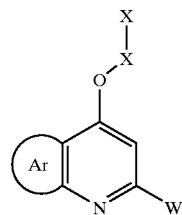

and the pharmaceutically acceptable salts thereof, wherein:

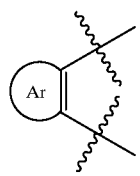

represents:

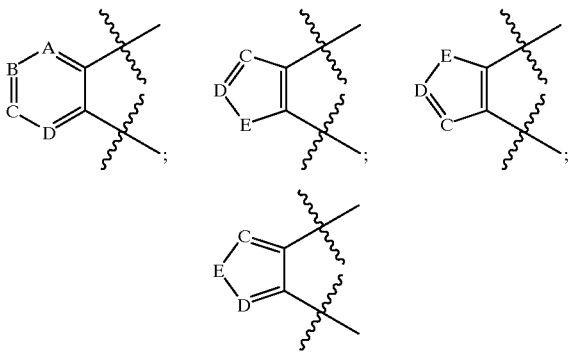

wherein:
A, B, C, and D are independently nitrogen or $CR_1$, and E represents oxygen, sulfur or $NR_2$,
  wherein
    when Ar is a 6-membered ring, 1 or 2 of A, B, C, and D are nitrogen; and
    when Ar is a 5-membered ring, C and D are both $CR_1$ and E is nitrogen, sulfur, or $NR_2$,
  where
    $R_1$, at each occurrence, is independently selected from the group consisting of hydrogen, halogen, cyano, halo($C_{1-6}$)alkyl, halo($C_{1-6}$)alkoxy, hydroxy, $C_{1-6}$ alkyl, amino, mono and di($C_{1-6}$)alkylamino, and $C_{1-6}$ alkoxy; and
    $R_2$ is selected from the group consisting of hydrogen, halogen, cyano, halo($C_1$–$C_6$)alkyl, halo($C_1$–$C_6$)alkoxy, hydroxy, $C_{1-6}$ alkyl, amino, and mono or di($C_1$–$C_6$)alkylamino;
W is selected from the group consisting of aryl, heteroaryl, and heterocycloalkyl, each of which is unsubstituted or substituted with one or more $R_3$; and
Q is selected from the group consisting of aryl, heteroaryl, and heterocycloalkyl, wherein each is unsubstituted or substituted with one or more of $R_4$;
  $R_3$ and $R_4$ at each occurrence are independently selected from the group consisting of hydrogen, halogen, hydroxy, —$OR_6$, —$NO_2$, —CN, —$SO_2NH_2$, —$SO_2NHR_6$, —$SO_2N(R_6)_2$, amino, —$NHR_6$, —$N(R_6)_2$, —$N(R_6)CO(R_6)$, —$N(R_6)CO_2(R_6)$, —$CONH_2$, —$CONH(R_6)$, —$CON(R_6)_2$, —$CO_2(R_6)$, —$S(R_6)$, $SO(R_6)$, —$SO_2(R_6)$, and $R_7$, wherein
    $R_6$, at each occurrence, is independently selected from the group consisting of $C_{1-8}$ alkyl, $C_{2-8}$ alkenyl, $C_{2-8}$ alkynyl, $C_{3-8}$ cycloalkyl, $C_{3-8}$ cycloalkenyl, and $C_{5-9}$ cycloalkynyl, each of which is unsubstituted or substituted with one or more substituents selected from the group consisting of hydroxy, oxo, halogen, amino, $C_{1-8}$ alkoxy, and $C_{1-8}$ alkyl,
    $R_7$ at each occurrence is independently selected from the group consisting of $C_{1-8}$ alkyl, $C_{1-8}$ alkenyl, $C_{1-8}$ alkynyl, $C_{3-8}$ cycloalkyl, $C_{3-8}$ cycloalkenyl, and $C_{5-9}$ cycloalkynyl, each of which is unsubstituted or substituted with one or more substituents selected from the group consisting of hydroxy, oxo, halogen, —$OR_6$, $C_{1-6}$alkyl, —$NO_2$, —CN, —$SO_2NH_2$, —$SO_2NHR_6$, —$SO_2N(R_6)_2$, amino, —$NHR_6$, —$N(R_6)_2$, —$N(R_6)CO(R_6)$, —$N(R_6)CO_2(R_6)$, —$CONH_2$, —$CONH(R_6)$, —$CON(R_6)_2$, —$CO_2H$, —$CO_2(R_6)$, —$S(R_6)$, —$SO(R_6)$, —$SO_2(R_6)$, and $NR_aR_b$, wherein
      each $NR_aR_b$ independently forms a monocyclic or bicyclic ring each of which may contain one or more double bonds, or one or more of oxo, O, S, SO, $SO_2$, NH, or $N(R_2)$, wherein $R_2$ is defined above and independently selected at each occurrence; or
Q is a group of the formula $NR_8R_9$ wherein
  $R_8$ and $R_9$ are independently hydrogen or $R_7$; or
  $R_8$, $R_9$ and the nitrogen to which they are attached form a heterocycloalkyl ring having from 5 to 8 ring atoms and where 1 or 2 of the ring atoms are selected from N, S, and O, with remaining ring members being carbon, CH, or $CH_2$, which heteroacycloalkyl ring is unsubstituted or substituted with one or more independently selected $R_4$ groups; and
X is —$(CH_2)_n$— or —$(CH_2)_n(C=O)$—, wherein each n is independently 1, 2, or 3.
The invention also provides compounds of Formula II

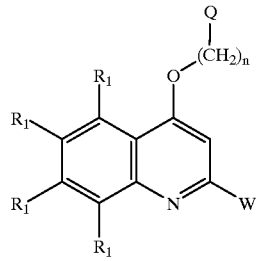

II and the pharmaceutically acceptable salts thereof, wherein:
W, Q, n, and each $R_1$ are as defined for Formula I, above.
In another aspect, the invention provides intermediates useful for preparing the compounds of Formulas I and II.
In a further aspect, the invention provides methods for making compounds of Formula I and II.

DETAILED DESCRIPTION OF THE INVENTION

In preferred compounds of Formula I and Formula II shown above, Ar is unsubstituted, i.e., $R_1$ is hydrogen. Also for preferred compounds of Formula I, X is either —$CH_2$— or —$CH_2(C=O)$—, and for preferred compounds of Formula II, X is preferably —$CH_2(C=O)$—.

In preferred compounds of Formula I and Formula II, Q is phenyl, thienyl, benzothienyl, pyridyl, piperidinyl, piperazinyl, quinolyl, pyrazinyl, pyrimidyl, imidazolyl, benzimidazolyl, furanyl, morpholinyl, benzofuranyl, thiazolyl, benzothiazolyl, isoxazolyl, oxadiazolyl, isothiazolyl, benzisothiazolyl, triazolyl, tetrazolyl, pyrrolyl, pyrrolidinyl, imidazolidinyl, imidazolinyl, isoxazolinyl, isoxazolidinyl, oxazolinyl, oxazolidinyl, indolyl, pyrazolyl, or benzopyrazolyl, each of which is optionally substituted.

Suitable substituents on Q include one or more of halogen, hydroxy, —$OR_6$, —$NO_2$, —CN, —$SO_2NH_2$, —$SO_2NHR_6$, —$SO_2N(R_6)_2$, amino, —$NHR_6$, —$N(R_6)_2$, —$N(R_6)CO(R_6)$, —$N(R_6)CO_2(R_6)$, —$CONH_2$, —$CONH(R_6)$, —$CON(R_6)_2$, —$CO_2(R_6)$, —$S(R_6)$, —$SO(R_6)$, —$SO_2(R_6)$, and $R_7$, wherein
  $R_6$, at each occurrence, is independently selected from the group consisting of $C_{1-8}$ alkyl, $C_{2-8}$ alkenyl, $C_{2-8}$ alkynyl, $C_{3-8}$ cycloalkyl, $C_{3-8}$ cycloalkenyl, and $C_{5-9}$ cycloalkynyl, each of which is unsubstituted or substituted with one or more substituents selected from the group consisting of hydroxy, oxo, halogen, amino, $C_{1-8}$ alkoxy, and $C_{1-8}$ alkyl, $R_7$ at each occurrence is independently selected from the group consisting of $C_{1-8}$ alkyl, $C_{1-8}$ alkenyl, $C_{1-8}$ alkynyl, $C_{3-8}$ cycloalkyl, $C_{3-8}$ cycloalkenyl, and $C_{5-9}$ cycloalkynyl, each of which is unsubstituted or substituted with one or more substituents selected from the group consisting of hydroxy, oxo, halogen, —$OR_6$, $C_{1-6}$alkyl, —$NO_2$, —CN, —$SO_2NH_2$, —$SO_2NHR_6$, —$SO_2N(R_6)_2$, amino, —$NHR_6$, —$N(R_6)_2$, —$N(R_6)CO(R_6)$, —$N(R_6)CO_2(R_6)$, —$CONH_2$, —$CONH(R_6)$, —$CON(R_6)_2$, —$CO_2H$, —$CO_2(R_6)$, —$S(R_6)$, —$SO(R_6)$, —$SO_2(R_6)$, and $NR_aR_b$, wherein each $NR_aR_b$ independently forms a monocyclic or bicyclic ring each of which may contain one or more double bonds, or one or more of oxo, O, S, SO, $SO_2$, NH, or $N(R_2)$, wherein $R_2$ carries the same definition as set forth above with respect to Formula I and is independently selected at each occurrence.

For more preferred compounds of Formula I and Formula II, Q is chosen from phenyl, pyridyl, pyrimidinyl, pyrazolyl, triazolyl, imidazolyl, pyrrolyl, piperidinyl, and pyrrolidinyl, each of which is unsubstituted or substituted with from 1 to 3 substituents independently selected from halogen, hydroxy, $C_{1-6}$alkoxy, —CN, amino, mono- and di($C_{1-6}$)alkylamino, and $C_{1-6}$ alkyl which is unsubstituted or substituted with 1 or more substituents chosen from hydroxy, oxo, amino, halogen, $C_{1-6}$alkyl, and $C_{1-6}$alkoxy, and mono- and di($C_{1-6}$)alkylamino.

In preferred compounds of Formula I and Formula II, W is phenyl, naphthyl, thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl or benzopyrazolyl each of which is optionally substituted. More preferably W is phenyl or pyridyl, each of which is optionally substituted. Other preferred compounds of Formula I and II are those where W is pyridyl substituted with $C_1$–$C_3$ alkyl, amino, mono- or di($C_1$–$C_3$)alkylamino, halogen, preferably chloro or fluoro, hydroxy, or $C_1$–$C_3$ alkoxy. Still other preferred compounds of Formula I and II are those where W is phenyl substituted with $C_1$–$C_3$ alkyl, amino, mono- or di($C_1$–$C_3$)alkylamino, halogen, preferably chloro or fluoro, hydroxy, or $C_1$–$C_3$ alkoxy.

The invention specifically includes compounds and salts of Formula III

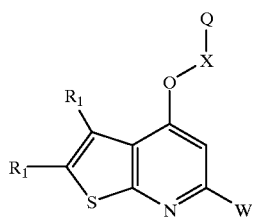

Formula III wherein $R_1$, Q, X, and W are as defined for Formula I.

Also included in the invention are compounds and salts of Formula IV

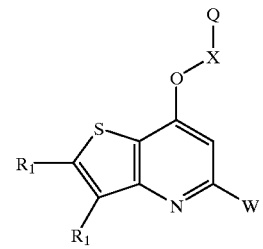

Formula IV wherein $R_1$, Q, X, and W are as defined for Formula I.

As a particular subformula of Formula IV, the invention includes compounds and salts of Formula V

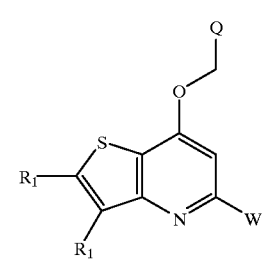

Formula V wherein $R_1$, Q, and W are as defined for Formula I.

As another subformula of Formula IV, the invention includes compounds and salts of Formula VI

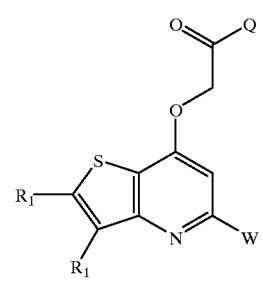

Formula VI wherein $R_1$, W, and Q are as defined for Formula I.

The invention is further directed to compounds and salts of Formula VII

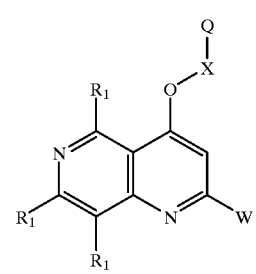

Formula VII wherein X, Q, $R_1$, and W are as defined for Formula I.

As a particular subformula of Formula VII the invention includes compounds and salts of Formula VIII Formula VIII

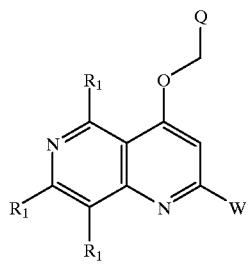

wherein Q, $R_1$, and W are as defined for Formula I.

The invention is further directed to compounds and salts of Formula IX

Formula IX

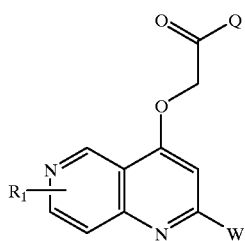

wherein $R_1$, Q, and W are as defined for Formula I

For each of Formula III—Formula IX preferred compounds and salts are those wherein W is phenyl or pyridyl each of which is unsubstituted or substituted with from 1 to 3 substituents independently selected from halogen, hydroxy, $C_{1-6}$alkoxy, -nitro, —CN, —$SO_2NH_2$, —$SO_2NHR_2$, —$SO_2N(C_{1-6}alkyl)_2$, amino, —$NHC_{1-6}$alkyl, —$N(C_{1-6}alkyl)_2$, —$CONH_2$, —$N(C_{1-6}alkyl)CO(C_{1-6}alkyl)$, —$N(C_{1-6}alkyl)CO_2(C_{1-6}alkyl)$, —$CON(C_{1-6}alkyl)_2$, —$CONH(C_{1-6}alkyl)$, —$CO_2(C_{1-6}alkyl)$—$S(C_{1-6}alkyl)$, —$SO(C_{1-6}alkyl)$, —$SO_2(C_{1-6}alkyl)$, and $C_{1-6}$alkyl which is unsubstituted or substituted with one or more substituents independently selected from hydroxy, halogen, and amino.

Also for each of Formula III—Formula IX preferred compounds and salts are those wherein:

Q is selected from phenyl, pyridyl, pyrimidinyl, pyrazolyl, triazolyl, imidazolyl, pyrrolyl, piperidinyl, and pyrrolidinyl, each of which is unsubstituted or substituted with from 1 to 3 substituents independently selected from: halogen, hydroxy, $C_{1-6}$alkoxy, —CN, amino, mono- and di($C_{1-6}$)alkylamino, and $C_{1-6}$ alkyl which is unsubstituted or substituted with 1 or more substituents chosen from hydroxy, oxo, amino, halogen, $C_{1-6}$alkoxy, and mono- and di($C_{1-6}$) alkylamino; or Q is a group of the formula $NR_8R_9$ wherein:

$R_8$ and $R_9$ are independently hydrogen or $C_{1-6}$ alkyl which is unsubstituted or substituted with 1 or more substituents chosen from hydroxy, oxo, amino, halogen, and $C_{1-6}$alkoxy, and mono- and di($C_{1-6}$)alkylamino; or $R_8$, $R_9$ and the nitrogen to which they are attached form a pyrrolidinyl or piperidinyl ring which is unsubstituted or substituted with from 1 to 3 substituents independently selected from halogen, hydroxy, $C_{1-6}$alkoxy, —CN, amino, mono- and di($C_{1-6}$)alkylamino, and $C_{1-6}$ alkyl which is unsubstituted or substituted with 1 or more substituents chosen from hydroxy, oxo, amino, halogen, $C_{1-6}$alkoxy, and mono- and di($C_{1-6}$) alkylamino.

Preferred compounds and salts of Formula II (described above) are those wherein n is 1.

Other preferred compounds and salts of Formula II are those wherein n is 1 or 2, or more preferably n is 1; and W is phenyl or pyridyl each of which is unsubstituted or substituted with from 1 to 3 substituents independently selected from halogen, hydroxy, $C_{1-6}$alkoxy, -nitro, —CN, —$SO_2NH_2$, —$SO_2NHR_2$, —$SO_2N(C_{1-6}alkyl)_2$, amino, —$NHC_{1-6}$alkyl, —$N(C_{1-6}alkyl)_2$, —$N(C_{1-6}alkyl)CO(C_{1-6}alkyl)$, —$N(C_{1-6}alkyl)CO_2(C_{1-6}alkyl)$, —$CONH_2$, —$CONH(C_{1-6}alkyl)$, —$CON(C_{1-6}alkyl)_2$, —$CO_2$ ($C_{1-6}$alkyl), —$S(C_{1-6}alkyl)$, —$SO(C_{1-6}alkyl)$, —$SO_2(C_{1-6}alkyl)$, and $C_{1-6}$alkyl optionally substituted with one or more substituents independently selected from hydroxy, halogen, and amino.

Particularly preferred compounds and salts of Formula II are those wherein:

n is 1;

Q is selected from phenyl, pyridyl, pyrimidinyl, pyrazolyl, triazolyl, imidazolyl, pyrrolyl, piperidinyl, and pyrrolidinyl, each of which is unsubstituted or substituted with from 1 to 3 substituents independently selected from: halogen, hydroxy, $C_{1-6}$alkoxy, —CN, amino, mono- and di($C_{1-6}$)alkylamino, and $C_{1-6}$ alkyl which is unsubstituted or substituted with 1 or more substituents chosen from hydroxy, oxo, amino, halogen, $C_{1-6}$alkyl, and $C_{1-6}$alkoxy, and mono- and di($C_{1-6}$)alkylamino; and W is phenyl or pyridyl each of which is unsubstituted or substituted with from 1 to 3 substituents independently selected from halogen, hydroxy, $C_{1-6}$alkoxy, —CN, amino, —$NHC_{1-6}$alkyl, —$N(C_{1-6}alkyl)_2$, and $C_{1-6}$alkyl optionally substituted with one or more substituents independently selected from hydroxy, halogen, and amino.

Specific compounds of Formula I include

5-Phenyl-7-[(3-pyridyl)methyloxy])-thieno[3,2-b] pyridine;

(R)-4-[[(2-Phenyl-4-quinolinyl)oxy]acetyl]-2-hydroxymethyl-pyrrolidine;

N,N-Diethyl-2-[(5-phenylthieno[3,2-b]pyridiyl)oxy]-acetamide

N,N-Diethyl-2-[[5-(2-fluorophenyl)thieno[3,2-b] pyridiyl]oxy]-acetamide;

N,N-Diethyl-2-[[5-(4-fluorophenyl)thieno[3,2-b] pyridiyl]oxy]-acetamide;

5-(4-Fluorophenyl)-7-[(4-pyridyl)methyloxy])-thieno[3, 2-b]pyridine;

7-[(3-(1-H-1,2,3-triazol-4-yl-methyloxy)]-5-phenylthieno[3,2-b]pyridine;

7-[(3-(1-H-1,2,3-triazol-4-yl-methyloxy)]-2-(4-fluorophenyl)-4-quinoline;

(R)-1-(2-Hydroxymethyl-pyrrolidin-1-yl)-2-(5-phenyl-thieno[3,2-b]pyridin-7-yloxy)-ethanone;

4-(1-Methyl-1H-[1,2,3]triazol-4-ylmethoxy)-2-phenylquinoline;

(R)-2-[2-(5-Fluoro-pyridin-2-yl)-quinolin-4-yloxy]-1-(2-hydroxymethyl-pyrrolidin-1-yl)-ethanone;

7-(1-Methyl-1H-[1,2,3]triazol-4-ylmethoxy)-5-phenylthieno[3,2-b]pyridine;

2-Phenyl-4-(pyridin-3-ylmethoxy)-[1,6]naphthyridine (R)-2-[2-(4-fluoro-phenyl)-[1,6]naphthyridin-4-yloxy]-1-(2-hydroxymethyl-pyrrolidin-1-yl)-ethanone;

2-[2-(4-fluoro-phenyl)-[1,6]naphthyridin-4-yloxy]-1-pyrrolidin-1-yl-ethanone;

2-(2-Phenyl-[1,6]naphthyridin-4-yloxy)-1-pyrrolidin-1-yl-ethanone;

4-(1-Methyl-1H-[1,2,3]triazol-4-ylmethoxy)-2-(4-fluoropyrid-2-yl)-quinoline;

7-(1-Methyl-1H-[1,2,3]triazol-4-ylmethoxy)-5-pyrid-2-yl-thieno[3,2-b]pyridine;

N,N-Diethyl-2-[5-(3-fluoro-pyridin-2-yl]-thieno[3,2-b]pyridin-7-yloxy)-acetamide;

N,N-Diethyl-2-[5-(5-fluoro-pyridin-2-yl]-thieno[3,2-b]pyridin-7-yloxy)-acetamide;

5-(4-Fluoro-pyridin-2-yl)-7-(pyridin-4-ylmethoxy)-thieno[3,2-b]pyridine;

7-(1H-[1,2,3]triazol-4-ylmethoxy)-5-(4-fluoro-pyrid-2-yl)-thieno[3,2-b]pyridine;

N,N-Diethyl-2-(5-pyridin-2-yl)-thieno[3,2-b]pyridin-7-yloxy)-acetamide;

5-Pyridin-2-yl-7-(pyridin-4-ylmethoxy)-thieno[3,2-b]pyridine; and (R)-2-[2-(5-Fluoro-pyridin-2-yl)-[1,6]naphthyridin-4-yloxy]-1-(2-hydroxymethyl-pyrrolidin-1-yl)-ethanone The invention also encompasses compounds of Formula X

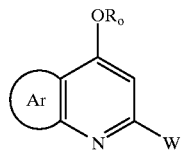

where
R$_o$ is hydrogen, C$_1$–C$_6$ alkyl, C$_1$–C$_6$ alkoxy(C$_1$–C$_6$)alkyl, C$_1$–C$_6$alkylthio(C$_1$–C$_6$)alkyl, allyl, phenacyl, cyclohexyl, benzyl, o-nitrobenzyl, 9-anthrylmethyl, 4-picolyl, t-butyldimethylsilyl, C$_1$–C$_6$ alkoxy(C$_1$–C$_6$) alkoxy(C$_1$–C$_6$)alkyl, or arylacyl, arylpivaloyl, arylbenzoyl, aryl 9-fluorenecarbonyl, arylmethyloxycarbonyl, C$_1$–C$_6$ acyl; aryl 2,2,2-trichloroethoxycarbonyl, aryl vinyl oxycarbonyl, aryl benzyloxy carbonyl, aryl methanesulfonyl; and the Ar ring and W carry the same definitions as set forth above for Formula I.

Preferred R$_o$ groups are hydrogen, C$_1$–C$_6$ alkyl, methoxymethyl, methylthiomethyl, allyl, phenacyl, cyclohexyl, benzyl, o-nitrobenzyl, 9-anthrylmethyl, 4-picolyl, t-butyldimethylsilyl, and 2-methoxyethoxymethyl. A particularly preferred R$_o$ group is hydrogen.

Specific compounds of formula X include those where Ar is Ar-1

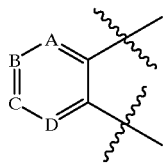

where B is nitrogen and A, C, and D are CR$_1$ where each R$_1$ is independently defined as above for Formula I.

Other specific compounds of Formula X include those where Ar is Ar-1 and A is nitrogen and B, C, and D represent CR$_1$.

Other specific compounds of formula X include those where Ar is Ar-2, Ar-3, or Ar-4

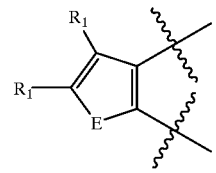

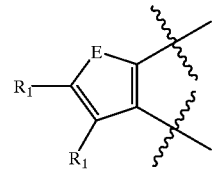

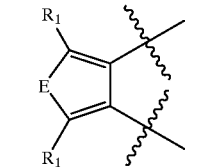

where E is NR$_2$, oxygen, or sulfur, and R$_1$ and R$_2$ are as defined above for Formula I.

Preferred compounds include those where Ar is Ar-3 and E is sulfur.

Preferred compounds of formula X also include those where W is pyridyl or phenyl, each of which is preferably unsubstituted or disubstituted, more preferably monosubstituted, independently with halogen, more preferably fluoro or chloro, hydroxy, C$_1$–C$_3$ alkyl, or C$_1$–C$_3$ alkoxy, preferably methoxy or ethoxy. A highly preferred pyridyl group is 2-pyridyl. Other preferred W groups include phenyl optionally substituted with halogen, more preferably fluoro or chloro, C$_1$–C$_3$ alkyl, hydroxy, or C$_1$–C$_3$ alkoxy, preferably methoxy or ethoxy. Particularly preferred W substituents include fluoro, chloro, hydroxy, and methoxy.

Specific compounds of Formula X include 5-(4-Fluorophenyl)-thieno[3,2-b]pyridin-7-ol;

6-(4-Fluorophenyl)-thieno[2,3-b]pyridin-4-ol;

6-(4-Fluorophenyl)-1H-pyrrolo[2,3-b]pyridin-4-ol;

5-(6-Fluoro-pyridin-3-yl)-thieno[3,2-b]pyridin-7-ol;

5-(5-fluoro-pyridin-2-yl)-thieno[3,2-b]pyridin-7-yl butyrate;

2-(4-fluoro-phenyl)-quinolin-4-yl acetate;

2-Pyridin-3-yl-quinolin-4-ol;

5-Phenyl-thieno[3,2-b]pyridin-7-ol;

2-Phenyl-quinolin-4-ol;

5-(2-Fluoro-phenyl)-thieno[3,2-b]pyridin-7-ol;

2-(4-Fluoro-phenyl)-quinolin-4-ol;

2-(5-Fluoro-pyridin-2-yl)-quinolin-4-ol;

2-(5-Fluoro-pyridin-2-yl)-[1,6]naphthyridin-4-ol;

2-(4-Fluoro-phenyl)-[1,6]naphthyridin-4-ol;

2-Phenyl-[1,6]naphthyridin-4-ol;

2-Pyridin-2-yl-[1,6]naphthyridin-4-ol;

5-(3-Fluoro-pyridin-2-yl)-thieno[3,2-b]pyridin-7-ol;

5-(5-Fluoro-pyridin-2-yl)-thieno[3,2-b]pyridin-7-ol;

6-Phenyl-thieno[2,3-b]pyridin-4-ol;

2-(3-Fluoro-pyridin-2-yl)-[1,6]naphthyridin-4-ol;
5-Pyridin-2-yl-thieno[3,2-b]pyridin-7-ol;
2-(5-Chloro-pyridin-2-yl)-quinolin-4-ol;
2-(5-Bromo-pyridin-2-yl)-[1,6]naphthyridin-4-ol;
2-(4-Chloro-phenyl)-[1,6]naphthyridin-4-ol;
5-(3-Chloro-2-methyl-pyridin-2-yl)-thieno[3,2-b]pyridin-7-ol; and
5-(5-Chloro-2-ethyl-pyridin-2-yl)-thieno[3,2-b]pyridin-7-ol.

This invention provides aryl fused oxypyridine derivatives that bind to the benzodiazepine site of $GABA_A$ receptors, including human $GABA_A$ receptors. This invention also includes such compounds that bind with high selectivity to the benzodiazepine site of $GABA_A$ receptors, including human $GABA_A$ receptors.

The invention further comprises methods of treating patients in need of such treatment with an amount of a compound of the invention sufficient to alter the symptoms of a CNS disorder. Compounds of the inventions that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases, conditions and disorders that can be treated using compounds and compositions according to the invention include:

Depression, e.g. depression, atypical depression, bipolar disorder, depressed phase of bipolar disorder.

Anxiety, e.g. general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

The invention also provides pharmaceutical compositions comprising compounds of the invention, including packaged pharmaceutical compositions for treating disorders responsive to $GABA_A$ receptor modulation, e.g., treatment of anxiety, depression, sleep disorders or cognitive impairment by $GABA_A$ receptor modulation. The packaged pharmaceutical compositions include a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

In a separate aspect, the invention provides a method of potentiating the actions of other CNS active compounds, which comprises administering a therapeutically effective amount of a compound of the invention in combination with another CNS active compound. Such CNS active compounds include, but are not limited to the following: for anxiety, serotonin receptor (e.g. 5-HTLA) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the $GABA_A$ receptor ligand 3-(5-methylisoxazol-3-yl)-6-(1-methyl-1,2,3-triazol-4-yl)methyloxy-1,2,4-triazolo [3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The invention also pertains to methods of inhibiting the binding of benzodiazepine compounds, such as Ro15-1788, to the $GABA_A$ receptors which methods involve contacting a compound of the invention with cells expressing $GABA_A$ receptors, wherein the compound is present at a concentration sufficient to inhibit benzodiazepine binding to $GABA_A$ receptors in vitro. This method includes inhibiting the binding of benzodiazepine compounds to $GABA_A$ receptors in vivo, e.g., in a patient given an amount of a compound of Formula I or Formula II that would be sufficient to inhibit the binding of benzodiazepine compounds to $GABA_A$ receptors in vitro. In one embodiment, such methods are useful in treating benzodiazepine drug overdose. The amount of a compound that would be sufficient to inhibit the binding of a benzodiazepine compound to the $GABA_A$ receptor may be readily determined via an $GABA_A$ receptor binding assay, such as the assay described in Example 30. The $GABA_A$ receptors used to determine in vitro binding may be obtained from a variety of sources, for example from preparations of rat cortex or from cells expressing cloned human $GABA_A$ receptors.

The invention also pertains to methods for altering the signal-transducing activity, particularly the chloride ion conductance of $GABA_A$ receptors, said method comprising exposing cells expressing such receptors to an effective amount of a compound of the invention. This method includes altering the signal-transducing activity of $GABA_A$ receptors in vivo, e.g., in a patient given an amount of a compound of Formula I or Formula II that would be sufficient to alter the signal-transducing activity of $GABA_A$ receptors in vitro. The amount of a compound that would be sufficient to alter the signal-transducing activity of $GABA_A$ receptors may be determined via a $GABA_A$ receptor signal transduction assay, such as the assay described in Example 31.

The $GABA_A$ receptor ligands provided by this invention and labeled derivatives thereof are also useful as standards and reagents in determining the ability of a potential pharmaceutical to bind to the $GABA_A$ receptor.

Radiolabeled derivatives of the compounds of this invention are also useful as radiotracers for positron emission tomography (PET) imaging or for single photon emission computerized tomography (SPECT).

The compounds of the invention may have asymmetric centers; this invention includes all of the stereoisomers and optical isomers as well as mixtures thereof.

In addition, compounds with carbon-carbon double bonds may occur in Z- and E- forms; all such isomeric forms of the compounds are included in the invention.

When any variable (e.g. $C_{1-6}$ alkyl, $C_{1-8}$ alkyl, $R_1$, W, n, Ar, G or Q) occurs more than one time in any formula herein, its definition on each occurrence is independent of its definition at every other occurrence.

As used herein, the term "alkyl" includes those alkyl groups of a designed number of carbon atoms. Alkyl groups may be straight, or branched. Examples of "alkyl" include methyl, ethyl, propyl, isopropyl, butyl, iso-, sec- and tert-butyl, pentyl, hexyl, heptyl, 3-ethylbutyl, and the like. When substituted, alkyl groups of the invention are understood to be substituted in substitutable positions with any of the specifid substituents groups.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl. The aryl groups herein are unsubstituted or, as specified, substituted in one or more substitutable positions with various groups.

The terms "halogen" or "halo" indicate fluorine, chlorine, bromine, and iodine.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, mono-, di-, or tri-fluoromethyl, mono-, di-, or tri-chloromethyl, mono-, di-, tri-, tetra-, or penta-fluoroethyl, and mono-, di-, tri-, tetra-, or penta-chloroethyl. Typical haloalkyl groups will have 1 to about 8 carbon atoms, more typically 1 to about 6 carbon atoms.

"Haloalkoxy" represents a haloalkyl group as defined above with the indicated number of carbon atoms attached through an oxygen bridge.

The term "heterocycloalkyl," refers to a non-aromatic ring system containing at least one heteroatom selected from nitrogen, oxygen, and sulfur. The heterocycloalkyl ring may be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrolidinyl. The heterocycloalkyl groups herein are unsubstituted or, as specified, substituted in one or more substitutable positions with various substituents.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidinyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, triazolyl, and benzopyrazolyl. The heteroaryl groups herein are unsubstituted or, as specified, substituted in one or more substitutable positions with various substituents.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of Formula I and Formula II.

The invention also encompasses the acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I and Formula II.

The disclosures of all articles and references mentioned in this application, including patents, are incorporated herein by reference.

Those skilled in the art will recognize various synthetic methodologies that may be employed to prepare non-toxic pharmaceutically acceptable prodrugs of the compounds encompassed by Formula I and Formula II. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I or Formula II may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I or Formula II and a pharmaceutically acceptable carrier. One or more compounds of general Formula I or Formula II may be present in association with one or more non-toxic pharmaceutically acceptable carriers and/or diluents and/or adjuvants and if desired other active ingredients. The pharmaceutical compositions containing compounds of general Formula I or Formula II may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in a mixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example gum tragacanth, sodium carboxymethylcellulose, methylcellulose, hydropropylmethylcellulose, polyvinylpyrrolidone, sodium alginate, and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I or Formula II may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I or Formula II may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the compounds of may be added to the animal's feed or drinking water. It may be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have pharmacological properties that include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

Preparation of Compounds

A general illustration of the preparation of compounds of Formula I and Formula II in the invention is given in Scheme I.

Scheme I

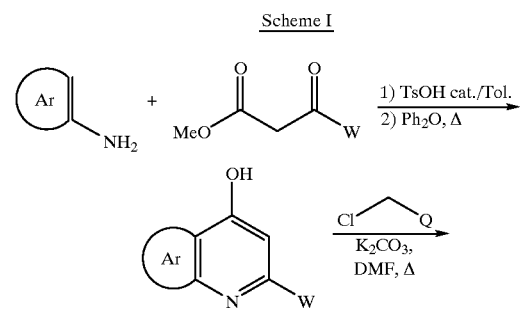

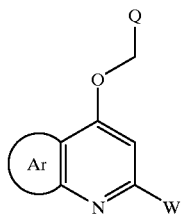

In Scheme I TsOH is p-toluenesulfonic acid, Tol. is toluene, Ph$_2$O is diphenylether, DMF is N,N-dimethylformamide, W is as defined for Formula I and Formula II, and particularly W may be phenyl or pyridyl which is unsubstituted or substituted with up to three independently selected substituents. Those skilled in the art will recognize that it may be necessary to utilize different solvents or reagents to achieve some of the above transformations.

The invention is illustrated further by the following examples. Those having skill in the art will recognize that the starting materials and reaction conditions may be varied and additional steps employed to produce compounds encompassed by the invention, as demonstrated by the following examples. In some cases, protection of reactive functionalities may be necessary to achieve some of the above transformations. In general, such need for protecting groups, as well as the conditions necessary to attach and remove such groups, will be apparent to those skilled in the art of organic synthesis.

EXAMPLES

Example 1

Preperation of 5-(4-Fluorophenyl)-thieno[3,2-b]pyridin-7-ol

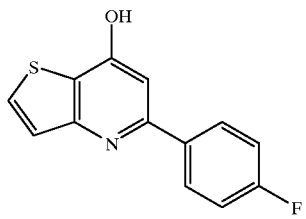

A mixture of 3-amino-2-thiophenecarboxylic acid (8 g, 49 mmol), ethyl 4-fluorobenzoylacetate (9.6 g, 49 mmol), and p-toluenesulfonic acid monohydrate (0.2 g, 1 mmol) in toluene (100 mL) is refluxed for 20 hours in a flask equipped with a Dean-Stark water trap. The mixture is cooled to room temperature and the precipitate filtered and washed with diethyl ether. The solid is dissolved in diphenyl ether (80 mL) and heated at 240° C. for 2 hours. The reaction solution is then cooled to room temperature, diethyl ether added and the precipitate filtered and washed with diethyl ether to give 5-(4-fluorophenyl)-thieno[3,2-b]pyridin-7-ol as brown crystalline needles, m.p. 316–318° C.

Example 2
Preparation of 5-(4-Fluorophenyl)-7-[(2-pyridyl)-methyloxy]-thieno[3,2-b]pyridine

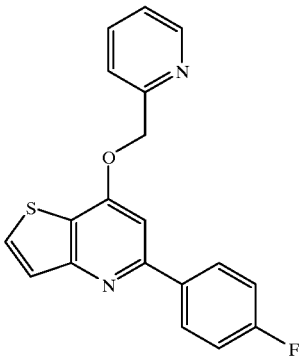

A mixture of 5-(4-fluorophenyl)-thieno[3,2-b]pyridin-7-ol (30 mg, 0.09 mmol), 2-picolyl chloride hydrochloride salt (30 mg) and potassium carbonate (100 mg) in DMF (2 mL) is heated at 100° C. for 2 hours. The reaction solution is cooled to room temperature, quenched with aqueous sodium bicarbonate solution and extracted several times with ethyl acetate. The combined ethyl acetate layers are dried over $Na_2SO_4$, filtered and concentrated. The residue is purified by preparative thin layer chromatography to give 5-(4-Fluorophenyl)-7-[(2-pyridyl)-methyloxy]-thieno[3,2-b]pyridine as white solid (compound 1).

LC-MS data: HPLC (min): 2.51 (HPLC method: Zorbax XDB-$C_{18}$ column, 4.6×30 mm, 3.5 μm particle size, 3 min gradient from 0 to 100% B with 0.5 min hold at 100% B. Solvent A: 95% $H_2O$-5%MeOH-0.05%TFA; Solvent B: 95%MeOH-5%$H_2O$-0.05%TFA). MS(ES$^+$): m/e 337.01.

Examples 3–26

The following compounds shown in Table I are prepared by methods analogous to that of Example 1–2. LC-MS data are given as HPLC retention times and (M+H)$^+$. The HPLC retention times of Table 1 may be obtained by the method given in Example 2.

TABLE 1

| Example No. | Ar | Q | W | Compound Name | HPLC (min) | MS (M + H)$^+$ |
|---|---|---|---|---|---|---|
| 3 | thieno[3,2-b] | 3-pyridyl | phenyl | 5-Phenyl-7-[(3-pyridyl)methyloxy])-thieno[3,2-b]pyridine | 1.64 | 318.95 |
| 4 | phenyl (benzo) | pyrrolidinyl-CH(CH2OH)-C(O)- | phenyl | (R)-4-[[(2-Phenyl-4-quinolinyl)oxy]acetyl]-2-hydroxymethyl-pyrrolidine | 1.76 | 363.08 |
| 5 | thieno[3,2-b] | -CH2-C(O)-NEt2 | phenyl | N,N-Diethyl-2-[(5-phenylthieno[3,2-b]pyridiyl)oxy]-acetamide | 1.92 | 341.03 |
| 6 | thieno[3,2-b] | -CH2-C(O)-NEt2 | 2-fluorophenyl | N,N-Diethyl-2-[[5-(2-fluorophenyl)thieno[3,2-b]pyridiyl]oxy]-acetamide | 2.01 | 359.17 |

TABLE 1-continued

| Example No. | Ar | Q | W | Compound Name | HPLC (min) | MS (M + H)+ |
|---|---|---|---|---|---|---|
| 7 | thiophene | C(O)NEt₂ | 4-fluorophenyl | N,N-Diethyl-2-[[5-(4-fluorophenyl)thieno[3,2-b]pyridiyl]oxy]-acetamide | 2.69 | 359.19 |
| 8 | thiophene | 4-pyridyl | 4-fluorophenyl | 5-(4-Fluorophenyl)-7-[(4-pyridyl)methyloxy])-thieno[3,2-b]pyridine | 2.40 | 336.94 |
| 9 | thiophene | 1H-1,2,3-triazol-4-yl | 4-fluorophenyl | 7-[(3-(1-H-1,2,3-triazol-4-yl-methyloxy)]-5-phenylthieno[3,2-b]pyridine | 1.99 | 245.99 |
| 10 | phenyl | 1H-1,2,3-triazol-4-yl | 4-fluorophenyl | 7-[(3-(1-H-1,2,3-triazol-4-yl-methyloxy)]-2-(4-fluorophenyl)-4-quinoline | 1.82 | 321.06 |
| 11 | thiophene | (R)-2-(hydroxymethyl)pyrrolidin-1-ylcarbonyl | phenyl | (R)-1-(2-Hydroxymethyl-pyrrolidin-1-yl)-2-(5-phenyl-thieno[3,2-b]pyridin-7-yloxy)-ethanone | | |
| 12 | phenyl | 1-methyl-1H-[1,2,3]triazol-4-yl | phenyl | 4-(1-Methyl-1H-[1,2,3]triazol-4-ylmethoxy)-2-phenyl-quinoline | | |

TABLE 1-continued

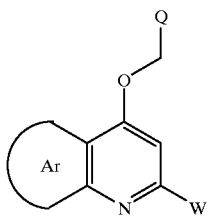

| Example No. | Ar | Q | W | Compound Name | HPLC (min) | MS (M + H)+ |
|---|---|---|---|---|---|---|
| 13 | benzene (1,2-disubst.) | C(O)-pyrrolidin-2-yl-CH2OH | 5-fluoro-pyridin-2-yl | (R)-2-[2-(5-Fluoro-pyridin-2-yl)-quinolin-4-yloxy]-1-(2-hydroxymethyl-pyrrolidin-1-yl)-ethanone | | |
| 14 | thiophene | 1-methyl-1H-[1,2,3]triazol-4-yl | phenyl | 7-(1-Methyl-1H-[1,2,3]triazol-4-ylmethoxy)-5-phenyl-thieno[3,2-b]pyridine | | |
| 15 | pyridine | pyridin-3-yl | phenyl | 2-Phenyl-4-(pyridin-3-ylmethoxy)-[1,6]naphthyridine | | |
| 16 | pyridine | C(O)-pyrrolidin-2-yl-CH2OH | 4-fluoro-phenyl | (R)-2-[2-(4-fluoro-phenyl)-[1,6]naphthyridin-4-yloxy]-1-(2-hydroxymethyl-pyrrolidin-1-yl)-ethanone | | |
| 17 | pyridine | C(O)-pyrrolidin-1-yl | 4-fluoro-phenyl | 2-[2-(4-fluoro-phenyl)-[1,6]naphthyridin-4-yloxy]-1-pyrrolidin-1-yl-ethanone | | |
| 18 | pyridine | C(O)-pyrrolidin-1-yl | phenyl | 2-(2-Phenyl-[1,6]naphthyridin-4-yloxy)-1-pyrrolidin-1-yl-ethanone | | |

TABLE 1-continued

| Example No. | Ar | Q | W | Compound Name | HPLC (min) | MS (M + H)+ |
|---|---|---|---|---|---|---|
| 19 | benzene | 1H-[1,2,3]triazol-4-yl | 5-fluoropyridin-2-yl | 4-(1-Methyl-1H-[1,2,3]triazol-4-ylmethoxy)-2-(4-fluoro-pyrid-2-yl)-quinoline | | |
| 20 | thiophene | 1-methyl-1H-[1,2,3]triazol-4-yl | pyridin-3,4-diyl | 7-(1-Methyl-1H-[1,2,3]triazol-4-ylmethoxy)-5-pyrid-2-yl-thieno[3,2-b]pyridine | | |
| 21 | thiophene | CH2C(O)NEt2 | 3-fluoropyridin-2-yl | N,N-Diethyl-2-[5-(3-fluoro-pyridin-2-yl)-thieno[3,2-b]pyridin-7-yloxy)-acetamide | | |
| 22 | thiophene | CH2C(O)NEt2 | 5-fluoropyridin-2-yl | N,N-Diethyl-2-[5-(5-fluoro-pyridin-2-yl)-thieno[3,2-b]pyridin-7-yloxy)-acetamide | | |
| 23 | thiophene | pyridin-4-yl | 5-fluoropyridin-2-yl | 5-(4-Fluoro-pyridin-2-yl)-7-(pyridin-4-ylmethoxy)-thieno[3,2-b]pyridine | | |
| 24 | thiophene | 1H-[1,2,3]triazol-4-yl | 5-fluoropyridin-2-yl | 7-(1H-[1,2,3]triazol-4-ylmethoxy)-5-(4-fluoro-pyrid-2-yl)-thieno[3,2-b]pyridine | | |
| 25 | thiophene | CH2C(O)NEt2 | pyridin-2-yl | N,N-Diethyl-2-(5-pyridin-2-yl)-thieno[3,2-b]pyridin-7-yloxy)-acetamide | | |

TABLE 1-continued

| Example No. | Ar | Q | W | Compound Name | HPLC (min) | MS (M + H)+ |
|---|---|---|---|---|---|---|
| 26 | (thiophene-fused) | pyridin-4-ylmethoxy | pyridin-2-yl | 5-Pyridin-2-yl-7-(pyridin-4-ylmethoxy)-thieno[3,2-b]pyridine | | |
| 27 | (pyridine-fused) | (2-hydroxymethyl-pyrrolidin-1-yl)-ethanone-O- | 5-fluoropyridin-2-yl | (R)-2-[2-(5-Fluoro-pyridin-2-yl)-[1,6]naphthyridin-4-yloxy]-1-(2-hydroxymethyl-pyrrolidin-1-yl)-ethanone | | |

Example 28
Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kan.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Tritium labeled probe compounds can also be prepared, when appropriate, by sodium borotritide reduction. Such preparations are also conveniently carried out as a custom radiolabeling by any of the suppliers listed in the preceding paragraph using the compound of the invention as substrate.

Example 29
Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding example.

Example 30
Binding Assay

The affinity and selectivity of compounds of this invention for the benzodiazepine site of the $GABA_A$ receptor is confirmed using the binding assay described in Thomas and Tallman (J. Bio. Chem. 1981; 156:9838–9842, and J. Neurosci. 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations containing 100 µl of tissue homogenate, 100 µl of radioligand, (0.5 nM $^{3}$H-RO15-1788 [$^{3}$H-Flumazenil], specific activity 80 Ci/mmol), and test compound or control (see below), and are brought to a total volume of 500 µl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^{3}$H RO15-1788 with 10 µM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve is obtained with up to 11 points spanning the compound concentration range from $10^{-12}$M to $10^{-5}$M obtained per curve by the method described above for determining percent inhibition. $K_i$ values are calculated according the Cheng-Prussof equation.

When tested in this assay compounds of the invention exhibit $K_i$ values of less than 1 µM, preferred compounds of the invention have $K_i$ values of less than 500 nM and more preferred compounds of the invention have $K_i$ values of less than 100 nM.

Example 31

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. *Xenopus Laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\beta_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 µM GABA is applied.

Compounds are evaluated against a GABA concentration that evokes <10% of the maximal evokable GABA current (e.g. 1 µM–9 µM). Each oocyte is exposed to increasing concentrations of compound in order to evaluate a concentration/effect relationship. Compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 µM RO15-1788, followed by exposure to GABA+1 µM RO15-1788 +test compound. Percent change due to addition of compound is calculated as described above. Any percent change observed in the presence of RO15-1788 is subtracted from the percent changes in current amplitude observed in the absence of 1 µM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A compound of the formula:

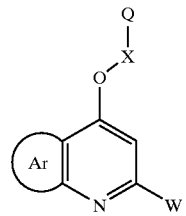

or a pharmaceutically acceptable salt thereof, wherein:

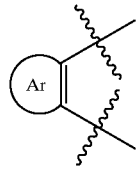

represents:

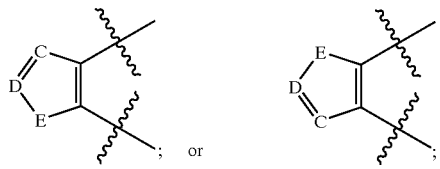

wherein:
C and D are $CR_1$, and
E represents sulfur,
where
$R_1$, at each occurrence, is independently selected from the group consisting of hydrogen, halogen, cyano, halo ($C_{1-6}$)alkyl, halo ($C_{1-6}$)alkoxy, hydroxy, $C_{1-6}$ alkyl, amino, mono and di($C_{1-6}$)alkylamino and $C_{1-6}$ alkoxy; and
$R_2$ is selected from the group consisting of hydrogen, halogen, cyano, halo($C_1$–$C_6$)alkyl, halo($C_1$–$C_6$) alkoxy, hydroxy, $C_{1-6}$ alkyl, amino, and mono or di($C_1$–$C_6$)alkylamino;
W is phenyl which is unsubstituted or substituted with 1, 2, 3, 4, or 5 $R_3$ groups or naphthyl which is unsubstituted or substituted with 1, 2, 3, 4, 5, 6, or 7 $R_3$ groups; and
Q is pyridinyl, which is unsubstituted or substituted with 1, 2, 3, or 4 $R_4$ groups;
$R_3$ and $R_4$ at each occurrence are independently selected from the group consisting of hydrogen, halogen hydroxy, —OR$_6$, —NO$_2$, —CN, —SO$_2$NH$_2$, —SO$_2$NHR$_6$, —SO$_2$N(R$_6$)$_2$, amino, —NHR$_6$, —N(R$_6$)$_2$, —N(R$_6$)CO(R$_6$), —N(R$_6$)CO$_2$(R$_6$), —CONH$_2$, —CONH(R$_6$), —CON(R$_6$)$_2$, —CO$_2$(R$_6$), —S(R$_6$), —SO(R$_6$), —SO$_2$(R$_6$), and R$_7$, wherein R$_6$, at each occurrence, is independently C$_{1-8}$ alkyl, which is unsubstituted or substituted with one or two substituents independently selected from the group consisting of hydroxy, oxo, halogen, amino, and C$_{1-8}$ alkoxy, R$_7$ at each occurrence is independently C$_{1-8}$ alkyl, which is unsubstituted or substituted with one or two substituents independently selected from the group consisting of hydroxy, oxo, halogen, —OR$_6$, —NO$_2$, —CN, —SO$_2$NH$_2$, —SO$_2$NHR$_6$, —SO$_2$N(R$_6$)$_2$, amino, —NHR$_6$, —N(R$_6$)$_2$, —N(R$_6$)CO(R$_6$), —N(R$_6$)CO$_2$(R$_6$), —CONH$_2$, —CONH(R$_6$), —CON(R$_6$)$_2$, —CO$_2$H, —CO$_2$(R$_6$), —S(R$_6$), —SO(R$_6$), and —SO$_2$(R$_6$), X is —(CH$_2$)$_n$— or —(CH$_2$)$_n$(C═O)—, wherein each n is independently 1, 2, or 3.

2. A compound or salt according to claim 1 of formula:

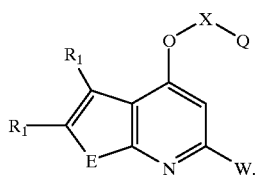

3. A compound or salt according to claim 2, wherein

W is phenyl, which is unsubstituted or substituted with from 1 to 3 substituents independently selected from halogen, hydroxy, C$_{1-6}$alkoxy, -nitro, —CN, —SO$_2$NH$_2$, —SO$_2$NHR$_6$, —SO$_2$N(C$_{1-6}$alkyl)$_2$, amino, —NHC$_{1-6}$alkyl, —N(C$_{1-6}$alkyl)$_2$, —N(C$_{1-6}$alkyl)CO(C$_{1-6}$alkyl), —N(C$_{1-6}$alkyl)CO$_2$(C$_{1-6}$alkyl), —CONH$_2$, —CONH(C$_{1-6}$alkyl), —CON(C$_{1-6}$alkyl)$_2$, —CO$_2$(C$_{1-6}$alkyl), —S(C$_{1-6}$alkyl), —SO(C$_{1-6}$alkyl), —SO$_2$(C$_{1-6}$alkyl), and C$_{1-6}$alkyl optionally substituted with one or more substituents independently selected from hydroxy, halogen, and amino.

4. A compound or salt according claim 2, wherein X is CH$_2$.

5. A compound or salt according to claim 4; wherein

Q is pyridyl, which is unsubstituted or substituted with from 1 to 3 substituents independently selected from halogen, hydroxy, C$_{1-6}$alkoxy, —CN, amino, mono- and di(C$_{1-6}$)alkylamino, and C$_{1-6}$ alkyl which is unsubstituted or substituted with 1 or two substituents independently chosen from hydroxy, oxo, amino, halogen, C$_{1-6}$alkyl, C$_{1-6}$alkoxy, and mono- and di(C$_{1-6}$) alkylamino; and W is phenyl which is unsubstituted or substituted with from 1 to 3 substituents independently selected from: halogen, hydroxy, C$_{1-6}$alkoxy, -nitro, —CN, —SO$_2$NH$_2$, —SO$_2$NHR$_6$, —SO$_2$N(C$_{1-6}$alkyl)$_2$, amino, —NHC$_{1-6}$alkyl, —N(C$_{1-6}$alkyl)$_2$, —N(C$_{1-6}$alkyl)CO(C$_{1-6}$alkyl), —N(C$_{1-6}$alkyl)CO$_2$(C$_{1-6}$alkyl), —CONH$_2$, —ONH(C$_{1-6}$alkyl), —CON(C$_{1-6}$alkyl)$_2$, —CO$_2$(C$_{1-6}$alkyl), —S(C$_{1-6}$alkyl), —SO(C$_{1-6}$alkyl), —SO$_2$(C$_{1-6}$alkyl), and C$_{1-6}$alkyl which is unsubstituted or substituted with one or two substituents independently selected from hydroxy, halogen, and amino.

6. A compound or salt according to claim 1 of formula:

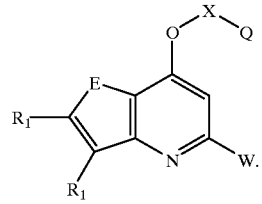

7. A compound or salt according to claim 6, wherein

W is phenyl which is unsubstituted or substituted with from 1 to 3 substituents independently selected from halogen, hydroxy, C$_{1-6}$alkoxy, -nitro, —CN, —SO$_2$NH$_2$, —SO$_2$NHR$_6$, —SO$_2$N(C$_{1-6}$alkyl)$_2$, amino, —NHC$_{1-6}$alkyl, —N(C$_{1-6}$alkyl)$_2$, —N(C$_{1-6}$alkyl)CO(C$_{1-6}$alkyl), —N (C$_{1-6}$alkyl)CO$_2$(C$_{1-6}$alkyl), —CONH$_2$, —ONH(C$_{1-6}$alkyl), —CON(C$_{1-6}$alkyl)$_2$, —CO$_2$(C$_{1-6}$alkyl), —S(C$_{1-6}$alkyl), —SO(C$_{1-6}$alkyl), —SO$_2$(C$_{1-6}$alkyl), and C$_{1-6}$alkyl which is unsubstituted or substituted with one or two substituents independently selected from hydroxy, halogen, and amino.

8. A compound or salt according to claim 7, wherein:

Q is pyridyl, which is unsubstituted or substituted with from 1 to 3 substituents independently selected from halogen, hydroxy, C$_{1-6}$alkoxy, —CN, amino, mono- and di(C$_{1-6}$)alkylamino, and C$_{1-6}$ alkyl which is unsubstituted or substituted with one or two substituents independently chosen from hydroxy, oxo, amino, halogen, C$_{1-6}$alkoxy, and mono- and di(C$_{1-6}$) alkylamino; and W is phenyl which is unsubstituted or substituted with from 1 to 3 substituents independently selected from halogen, hydroxy, C$_{1-6}$alkoxy, -nitro, —CN, —SO$_2$NH$_2$, —SO$_2$NHR$_6$, —SO$_2$N(C$_{1-6}$alkyl)$_2$, amino, —NHC$_{1-6}$alkyl, —N(C$_{1-6}$alkyl)$_2$, —N(C$_{1-6}$alkyl)CO(C$_{1-6}$alkyl), —N(C$_{1-6}$alkyl)CO$_2$(C$_{1-6}$alkyl), —CONH$_2$, —CONH(C$_{1-6}$alkyl), —CON(C$_{1-6}$alkyl)$_2$, —CO$_2$(C$_{1-6}$alkyl), —S(C$_{1-6}$alkyl), —SO(C$_{1-6}$alkyl), —SO$_2$(C$_{1-6}$alkyl), and C$_{1-6}$alkyl which is unsubstituted or substituted with one or two substituents independently selected from hydroxy, halogen, and amino.

9. A compound according to claim 1, which is 5-(4-Fluorophenyl)-7-[(2-pyridyl)-methyloxy]-thieno[3,2-b]pyridine.

10. A compound according to claim 1, which is 5-Phenyl-7-[(3-pyridyl)methyloxy]-thieno[3,2-b]pyridine.

11. A compound according to claim 1, which is 7-[(4-Pyridyl)methyloxy]-5-phenylthieno[3,2-b]pyridine.

12. A pharmaceutical composition comprising a compound or salt according to claim 1 combined with a pharmaceutically acceptable carrier or excipient.

13. A method for the treatment of anxiety, depression, or a sleep disorder, comprising administering a therapeutically effective amount of a compound or salt of claim 1 to a patient in need thereof.

14. A compound according to claim 1 of the formula

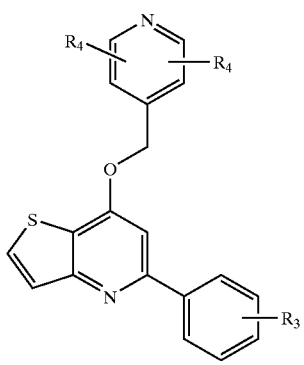

wherein $R_3$ is selected from the group consisting of $(C_1-C_6)$alkyl, $(C_1-C_6)$alkoxy, halogen, and OH; and $R_4$ at each occurrence is independently selected from the group consisting of hydrogen, halogen, hydroxy, alkoxy, —$NO_2$, —CN, —$SO_2NH_2$, —$SO_2NH(C_1-C_6)$alkyl, —$SO_2N((C_1-C_6)$alkyl$)_2$, amino, —$NH(C_1-C_6)$alkyl, —$N(99C_1-C_6)$al;kyl$)_2$, —$N(R_6)CO((C_1-C_6)$alkyl, —$N((C_1-C_6)$alkyl$)CO_2((C_1-C_6)$alkyl$)$, —$CONH_2$, —$CONH((C_1-C_6)$alkyl$)$, —$CON((C_1-C_6)$alkyl$)_2$, —$CO_2((C_1-C_6)$alkyl$)$, and $(C_1-C_6)$alkyl.

15. A compound according to claim 14, wherein $R_3$ is selected from the group consisting of $(C_1-C_4)$alkyl, $C_1-C_4)$alkoxy, halogen, and OH; and only one of the $R_4$ groups is hydrogen.

16. A compound according to claim 14, wherein $R_3$ is selected from the group consisting of $(C_1-C_4)$alkyl, $(C_1-C_4)$alkoxy, halogen, and OH; and one of the $R_4$ groups is halogen.

17. A compound according to claim 14, of the formula

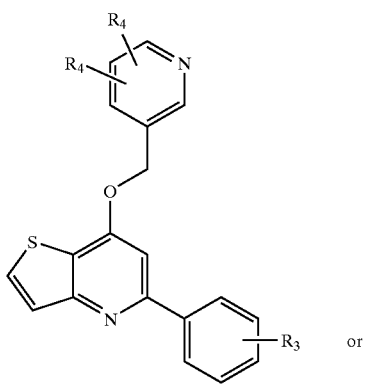

or

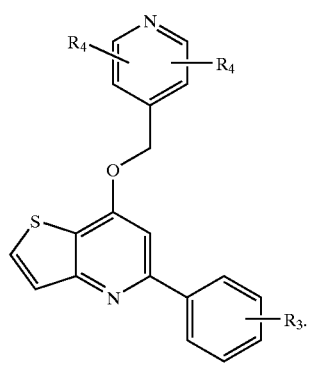

18. A compound according to claim 17, wherein $R_3$ is halogen.

* * * * *